United States Patent [19]

Khilnani

[11] Patent Number: 4,560,585
[45] Date of Patent: Dec. 24, 1985

[54] POISON RESISTANT COMBUSTIBLE GAS SENSOR

[75] Inventor: Gul Khilnani, Fremont, Calif.

[73] Assignee: Rexnord Inc., Brookfield, Wis.

[21] Appl. No.: 564,982

[22] Filed: Dec. 23, 1983

[51] Int. Cl.$^4$ .............................................. B05D 5/12
[52] U.S. Cl. .................... 427/103; 427/123;
427/125; 427/126.3; 427/126.4; 427/376.2;
427/376.3; 427/376.4; 427/376.6; 427/405;
427/419.2; 338/34; 422/97; 422/98
[58] Field of Search ................ 422/97, 98; 427/116,
427/123, 125, 126.3, 126.4, 103, 376.2, 376.3,
376.4, 376.6, 383.3, 383.7, 405, 419.2; 338/34

[56] References Cited

U.S. PATENT DOCUMENTS

| | | | |
|---|---|---|---|
| 3,092,799 | 6/1963 | Baker | 422/95 |
| 3,564,474 | 2/1971 | Firth et al. | 338/34 |
| 4,068,021 | 1/1978 | Allman | 427/116 |
| 4,072,467 | 2/1978 | Jones | 338/34 |
| 4,246,228 | 1/1981 | Jones et al. | 338/34 |

FOREIGN PATENT DOCUMENTS 2096321 10/1982 United Kingdom ................ 422/97

Primary Examiner—Richard Bueker
Attorney, Agent, or Firm—Richard C. Ruppin

[57] ABSTRACT

A combustible gas sensor element prepared by the process of applying, to a sheathed wire coil, separate coats of catalytic wash each heated in a furnace, separate and alternating coats of porous ceramic and platinum each heated by passing an electric current through the coiled wire filament, and separate coats of porous ceramic top coating, each heated by passing an electric current through the filament.

6 Claims, 6 Drawing Figures

POISON RESISTANT COMBUSTIBLE GAS SENSOR

BACKGROUND OF THE INVENTION

The present invention relates to a method for making a sensing element and a sensing element used in a catalytic combustible gas sensor and more particularly to a poison resistant sensing element of the resistive type used in atmospheres containing poisons, such as silicones, halogenated hydrocarbons, and organometallics, and a method for making the same.

The present invention is applicable generally to combustible gas sensors of the imbedded coiled wire filament type preferably of the kind described in U.S. Pat. Nos. 3,959,764 and 4,068,021, that is, a helically coiled filament coated with a refractory material, generally applied in a liquid form, which is then heated, e.g. in a furnace, so that the coating matures during the heating and sintering takes place to produce a dense sheath. The sintering process shrinks the coating and, at the same time, compresses the helical coil, to form a dense coated helical coil filament with an internal passage therethrough. Over this dense coating, a platinum catalyst is applied to oxidize combustible gases. A difficulty which has been experienced with sensors as described above is that they rapidly lose their response level when exposed to a catalytic poison.

Further, the problem with prior art devices, such as bead-type sensing elements as described in U.S. Pat. Nos. 3,200,011 and 4,123,225 is that they require immediate recalibration or replacement after exposure to a catalytic poison. These sensors operate very successfully in clean atmospheres, i.e. without loss of sensitivity, however, use in more hostile industrial environments results in irreversible loss of sensitivity or poisoning.

SUMMARY OF THE INVENTION

The present invention is directed to a poison resistant combustible gas sensor, and is summarized in the following objects:

First, to provide a multi-layered element of a combustible gas sensor having a porous non-catalytic ceramic sandwiched between platinum catalysts, and an outer coating of a porous ceramic resulting from fixing a mixture of alumina and liquid aluminum chloride. This outer coating acts as a sacrificial layer to react with and trap airborne poisons, such as silicone (RTV), tetraethyl lead (gasoline), organo-phosphates, carbon tetrachloride, and trichloroethylene.

Second, to provide an outer coating or layer on the combustible gas sensor element which retains high porosity, to allow diffusion of the combustible gases therethrough, even after trapping or decomposing a majority of the catalytic poisons.

Third, to provide surfaces for volatile halide compounds of platinum to decompose back to platinum thereby retarding loss of the catalysts.

Fourth, to provide a combustible gas sensor element having a plurality of catalytic layers which permits the inner layers to still react with the combustible gas after the outer layers are poisoned.

Fifth, to provide a combustible gas sensor having a minimal zero shift and a long term temperature stability.

The foregoing and other objectives, features and advantages of the present invention are accomplished by providing a combustible gas sensor element comprising a coiled wire filament of noble metal alloy having a refractory coating, which after maturation produces a dense refractory sheath, and a plurality of porous non-catalytic ceramic layers sandwiched between catalytic metal layers, on both the inner and outer surface of the sheathed wire filament.

The combustible gas sensor element may be prepared by the process of applying, to a sheathed wire coil, separate coats of catalytic wash each heated at a temperature of about 1650° F. in a furnace, separate and alternating coats of porous ceramic and platinum each heated by passing an electric current through the coiled wire filament, and separate coats of porous ceramic top coating, each heated by passing an electric current through the filament.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

The present invention is particularly adapted for use in environments where airborne poisons, such as silicone, are present. Generally, vapors from silicone-based products cause rapid deterioration of standard catalytic bead combustible gas sensors. Typically, a silicone concentration of less than one part per million (ppm) can cause the standard sensor to lose its sensitivity within minutes. The present invention, with its new dispersion and application of catalyst and ceramic, however, maintains its reliability and accuracy in the presence of silicone and other poisons. The low-mass helically wound sensor element offers increased resistance to mechanical shock, as well as more uniform heating and fast response in still air.

Figure 1:
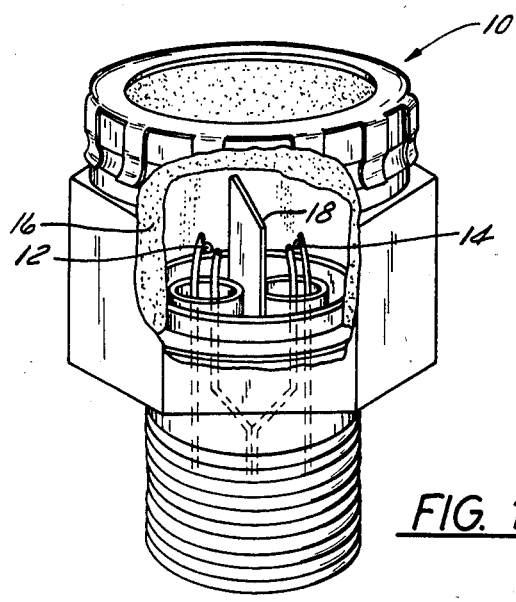
FIG. 1 is a perspective view of a combustible gas sensor, partly broken away to show the poison resistant sensor element of the present invention.

In accordance with the preferred embodiments of the invention, as shown in FIG. 1, there is depicted a combustible gas sensor 10 made up of two elements, an active or catalytic element 12 and an inactive or reference element 14, both of which are exposed to the atmosphere. The active/reference element pair 12, 14 is enclosed in a porous metallic cup 16, which can be stainless steel, or enclosed behind a disc of similar material. This cup 16 or disc, called a flame arrester, allows the diffusion of gas to and from the element pair, but prevents the igniton of the atmosphere outside the sensor in the event the combustible gas concentration exceeds its lower flammable limit.

Usually a thermal barrier 18 is placed between the element pair 12, 14 to prevent thermal interaction and to prevent the transfer of catalytic material from the active element to the surface of the reference element.

The sensor is connected into the electrical circuit of a gas detection system. Generally, the matched element pair 12, 14 complete a Wheatstone bridge arrangement.

Figure 2:
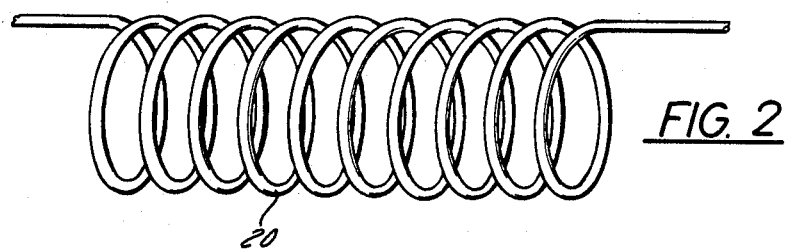
FIG. 2 is an elevational view of an uncoated coiled resistive element of the present invention.
Figure 3:
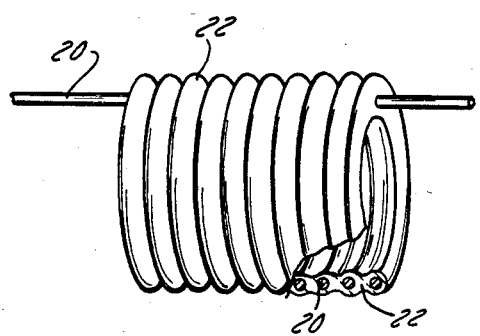
FIG. 3 is an elevational view, partly broken away and sectioned, of the resistive element in FIG. 2 after maturation of a coat of refractory material.

Referring now to FIGS. 2 and 3 of the drawings, there is depicted a helically wound conductive filament 20, made of a material such as platinum-iridium, whose electrical resistance varies with temperature. There are other suitable coil filaments, for example, a platinum-rhodium alloy. The helically coiled filament 20 is then sheathed in a refractory material 22 as described in U.S. Pat. No. 4,068,021 incorporated herein by reference.

Figure 4:
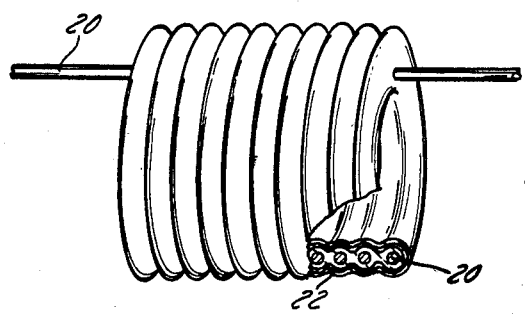
FIG. 4 is an elevational view, partly broken away and sectioned, of the coated coil in FIG. 3 after applying a plurality of separate and alternating layers of porous ceramic and platinum and a porous ceramic top coating.
Figure 5:
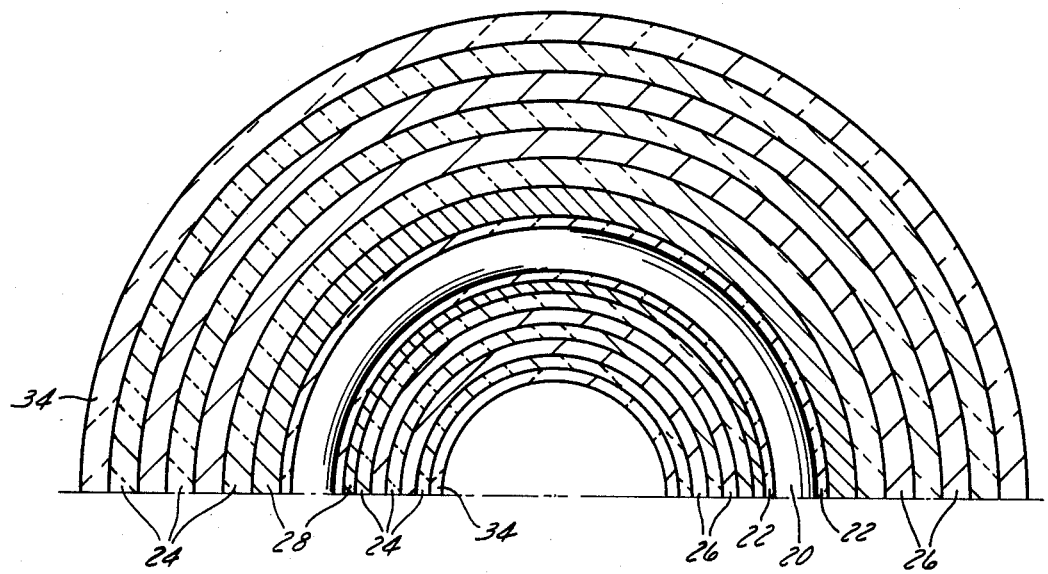
FIG. 5 is an enlarged view of a cross-section along the transverse axis of FIG. 4.
Figure 6:
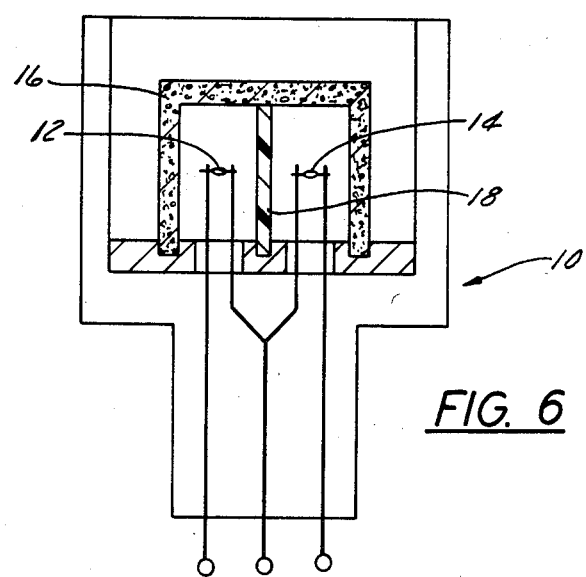
FIG. 6 is a schematic representation of a cross-section along the longitudinal axis of FIG. 5.

According to the present invention and referring now to FIGS. 4 and 5, the refractory sheath 22 is coated with a first layer of catalytic wash 28, then with alternating layers of porous non-catalytic ceramic 24 and layers of a platinum catalyst 26 or other noble metals or catalytic metals, such as, palladium, rhodium, ruthenium or rhenium or mixtures thereof. The element is then coated with a top layer 34 of porous ceramic which is used as a sacrificial layer to initially react with or trap airborne poisons.

In accordance with the preferred method of the invention, a catalytic wash in a liquid or paste form is formed by mixing in water a ceramic stock (5–10% $Al_2O_3$ by weight of the mixture) and a platinum stock (5–15% hexachloroplatinic acid by weight of the mixture). (The hexachloroplatinic acid contains 40% platinum metal, therefore the range of platinum in the mixture would be 2–6% by weight.) The catalytic wash is applied to the sheathed coil and is fired by heating, for example in a furnace at 1600°–1700° F. for a period of 5 to 25 minutes, preferably about 10 minutes. The first layer of catalytic wash 28 may include one or more coats, each applied as described above.

After the layer of catalytic wash 28 has been fired, alternating layers of mixture in water of a ceramic 24 (5–10% $Al_2O_3$ by weight of the mixture) and a mixture in water of a ceramic stock of a platinum catalyst 26 (5–25% hexachloroplatinic acid by weight of the mixture) are applied to the sheathed coil. The ceramic, an aqueous solution of alumina linde "B" ($Al_2O_3$), may be fired by applying a voltage to the coiled filament 20 to cure the ceramic solution and produce a porous ceramic layer on the element. The voltage of 2.0–3.0 V.d.c., preferably about 2.5 V.d.c., is applied for a period of from 1 to 3 minutes. However, a voltage of 2.5–3.5 V.d.c., preferably about 3.0 V.d.c., applied for a period of 2 minutes is generally applied to the outermost or final layer of the ceramic solution. The platinum catalyst, an aqueous solution of hexachloroplatinic acid hexahydrate ($H_2PtCl_6 \cdot 6H_2O$), 20% by weight mixed with a ceramic stock, may also be decomposed to form dispersed platinum particles by applying a voltage to the coiled filament 20 to heat the mixture. The preferred voltage is about 2.0 V.d.c., but may vary from 1.5 V.d.c. to 2.5 V.d.c., and is applied for a period of from 1 to 3 minutes. Generally, the catalytic wash layer 28 is comprised of two (2) coats.

The porous non-catalytic ceramic layer 24 and the platinum catalyst layer 26 may also include one or more coats. Generally, the porous non-catalytic ceramic layer 24 has two (2) coats, but the final layer has four (4) coats, while the platinum catalyst layer 26 has six (6) coats.

Finally, a top layer 34 is formed by mixing alumina (15–25% $Al_2O_3$ by weight of the mixture) with an aqueous solution of aluminum chloride (5–25% $AlCl_3$ by weight of the mixture) and ethylene glycol, and applying the mixture to the layered coil. The top layer mixture is dried and fired "in situ to render it porous" by applying a voltage of 2.5–3.5 V.d.c., preferably 3.0 V.d.c to the coiled filament, for a period of from 1 to 3 minutes. Generally, two (2) coats of mixture are applied to form the top layer 34.

A poison resistant element of the present invention, and a method of preparing the same, is further illustrated by, but not limited to, the following examples:

EXAMPLE 1

A helically coiled filament using a 90% platinum/10% iridium alloy coil is coated with refractory material as taught in U.S. Pat. No. 4,068,021. This sheathed coil is coated with two coats of catalytic wash which are oven dried and fired for 10 minutes at 1650° F. to effect liquid removal. This catalytic wash layer, comprising two coats, forms a basis for subsequent alternating layers of non-catalytic ceramic 24 and platinum catalyst 26. The catalytic wash is a mixture of ceramic stock and platinum stock as follows:

CERAMIC STOCK (11.76% $Al_2O_3$ by weight of the mixture)

| | |
|---|---|
| Alumina, Linde "B", 0.05 Micron ($Al_2O_3$) (Available from Union Carbide Co.) | 5.0 g |
| Aqueous Solution of METHOCEL MC, 2% by weight (Available from Dow Chemical Co.) | 10.0 ml |
| Deionized Water | 15.0 ml |
| Surfynol 104E, 0.05% by weight (Available from Air Products Inc.) | 7.5 ml |
| Igepal CO-880, 0.05% by weight (Available from GAF Corp.) | 7.5 ml |
| Defoamer T-109 (Available from Transchemco Inc.) | 2 drops |

PLATINUM STOCK

Aqueous solution of hexachloroplatinic acid hexahydrate ($H_2PtCl_6 6H_2O$) 20% by weight.

The ceramic stock was milled in a Lortone milling machine for 24 hours. The milled ceramic stock was then mixed with the platinum stock in a volume ratio of 1:1.

The sheathed coil with the catalytic wash layer 28, as described above, is then coated with two coats of ceramic to form non-catalytic ceramic layer 24. The coats of ceramic are heated by applying 2.5 V.d.c across the helical coil for 2 minutes. The following materials were used to prepare the aqueous solution of non-catalytic ceramic:

| | |
|---|---|
| Alumina, Linde "B", 0.05 Micron | 2.5 g |

-continued

| | |
|---|---|
| Aqueous Solution of METHOCEL MC, 2% by weight | 15.0 ml |
| Deionized Water | 10.0 ml |
| Surfynol 104E, 0.05% by weight | 7.5 ml |
| Igepal CO-880, 0.05% by weight | 7.5 ml |
| Defoamer T-109 | 2 drops |

The aqueous ceramic solution was milled in a Norton porcelain jar, one-half filled with ⅜ inch zirconia grinding media for 24 hours. The net alumina ($Al_2O_3$) in the ceramic is 5.88% by weight.

The aqueous solution of hexachloroplatinic acid hexahydrate ($H_2PtCl_6.6H_2O$) 20% by weight, mixed with ceramic stock is then applied to the sheathed coil with the layer of catalytic wash and the layer of non-catalytic ceramic as described above, to form a layer of platinum catalyst 26. Six coats of the mixture of ceramic stock and aqueous solution of hexachloroplatinic acid are applied and the mixture is cured and the hexachloroplatinic acid decomposed by applying 2.0 V.d.c. across the helical coil for 2 minutes, to form the catalytic layer 26.

Two more non-catalytic ceramic layers 24 and one more catalytic layer 26 are then alternately applied as described above. However, the final layer of non-catalytic ceramic is comprised of four coats, each heated by applying 3.0 V.d.c. across the helical coil for 2 minutes.

Finally, two coats of an aqueous ceramic solution are applied to form a top layer 34. The top layer 34, when cured, has a higher porosity than the other ceramic layers 24 and is made from a mixture of the following materials:

| | |
|---|---|
| Alumina, Gamma Baikalox, 0.05 Micron | 4.0 g |
| Aqueous Solution of Aluminum Chloride, 10% by weight ($AlCl_3$) | 8.0 ml |
| Ethylene Glycol | 8.0 ml |

In the above mixture, the alumina is approximately 21% by weight of the mixture and the aluminum chloride is approximately 4% by weight of the mixture. It may be noted that the term "Baikalox" is a registered trademark of the Baikowski International Corporation and identifies aluminum oxide sold by Baikowski. The aqueous solution of $AlCl_3$ and ethylene glycol were added to the alumina ($Al_2O_3$) to obtain a larger surface area and make it a highly porous top layer which allows the passage of flammable gases through the catalytic layer 26 underneath, whereas poison molecules are either trapped or decomposed within the alumina.

EXAMPLE 2

This example also uses a helically coiled filament coated with refractory material as taught in U.S. Pat. No. 4,068,021. This sheathed coil is then coated with a layer of two coats of non-catalytic ceramic, a catalytic wash layer, comprising two coats, and alternating layers of non-catalytic ceramic and platinum powder (platinum black).

The non-catalytic ceramic stock is the same as the ceramic stock used in the catalytic wash of Example 1. The catalytic wash is a mixture of the ceramic stock and platinum powder stock as follows:

| | |
|---|---|
| Platinum Powder (Pt. Black) | 4.0 g |
| Ceramic (as previously described) | 16.0 g |
| Surfynol 104E, 0.05% by weight | 4.0 g |

The platinum powder was prepared from an aqueous solution of hexachloroplatinic acid hexahydrate, ($H_2PtCl_6.6H_2O$) 10% by weight, which was reduced by treatment with an aqueous solution of 5% by weight sodium borohydride ($NaBH_4$) which results in the precipitation of finely divided platinum. The precipitate was decanted with deionized water, hot deionized water and isopropyl alcohol before it was dried in an oven at 100° C.

The platinum powder, ceramic stock and Surfynol 104E were weighed and poured into a nalgene 2 oz. polyethylene bottle half filled with ⅜" zirconium oxide media. The bottle was then placed in a Lortone Inc. rubberized jar and milled for four hours.

The sheathed coil is coated with two coats of ceramic to form a non-catalytic ceramic layer. The coats of ceramic are an aqueous solution as used in the catalytic wash, and are heated by applying 2.5 V.d.c across the helical coil for 2 minutes. The first layer of non-catalytic ceramic is then coated with a layer of two coats of catalytic wash, as described in Example 1.

The sheathed coil with the layer of ceramic and the layer of catalytic wash is then coated with a layer of aqueous non-catalytic ceramic. Two coats of the non-catalytic ceramic are applied and fired by applying 2.5 V.d.c. across the helical coil for 2 minutes each.

The aqueous solution of hexachloroplatinic acid, 20% by weight, mixed with ceramic stock, is then applied to the sheathed coil with the layer of ceramic, the layer of catalytic wash and the layer of non-catalytic ceramic as described above, to form a layer of platinum catalyst. Four coats of the aqueous solution of platinum are applied and fired by applying 2.0 V.d.c across the helical coil for 2 minutes, to form the catalytic layer.

Finally, two more non-catalytic ceramic layers and one more catalytic layer are then alternately applied as described above.

It is believed that the higher resistance to poisoning by the present invention is due to (1) the major portions of the poisons being trapped or decomposed in the top sacrificial layer by the highly porous ceramic layer, (2) the subsequent catalytic layers, which after the first catalytic layer becomes inactive, still oxidize combustible gases, thus providing the sensor with a long use life, and (3) the surfaces impeding any formation of volatile halide compounds of platinum.

The process of the present invention results in an embodiment which consists of a completely dispersed platinum catalyst in a highly porous alumina support, which maintains a uniform particle size to minimize any agglomeration or cluster compound formation, and also in a top sacrificial layer to trap or decompose airborne poisons, thus retarding the loss of the catalyst. Elements have been made by the inventive method that have exhibited excellent characteristics when exposed to most commonly known catalytic poisons.

I claim:

1. A method for producing a poison resistant active element for a combustible gas sensor comprising the steps of:

forming a filament of electrically conductive material having a resistance which varies with temperature into a helical coil;

coating said helical coil with a refractory material and heating said refractory material until sintering takes place to produce a dense gas-tight sheath;

applying a first layer in liquid mixture form of a combination ceramic material and catalytically active material to said sheath on the helical coil;

curing said first layer at a temperature in the range of 800° C. to 1100° C. from 2 minutes to 3 minutes;

applying a plurality of alternating layers in liquid mixture form of a non-catalytic ceramix material and a catalytically active material to said first cured layer on said helical coil;

curing the non-catalytic ceramic liquid mixture material of said plurality of alternating layers at a temperature in the range of 800° C. to 1100° C. from 2 minutes to 3 minutes, and curing the catalytically active liquid mixture material of said plurality of alternating layers at a temperature in the range of 800° C. to 900° C. from 2 minutes to 3 minutes;

applying a final layer of a liquid mixture containing aluminum chloride and aluminum oxide to the final one of the alternating layers; and curing said mixture layer of aluminum chloride and aluminum oxide at a temperature in the range of 800° C. to 1100° C. from 2 minutes to 3 minutes to form a cured final layer of non-catalytic porous aluminum oxide.

2. A method as recited in claim 1 wherein the ceramic material of said first layer in liquid mixture form is alumina within the range of 5% to 10% by weight of the mixture and the catalytically active material is platinum within the range of 2% to 6% by weight of the mixture.

3. A method as recited in claim 1 wherein the porous non-catalytic ceramic material of said plurality of alternating layers in liquid mixture form is alumina within the range of 5% to 10% by weight of the mixture.

4. A method as recited in claim 1 wherein said final layer of ceramic material is formed from a liquid mixture of alumina within the range of 15% to 25% by weight of the mixture and aluminum chloride within the range of 4% to 25% by weight of the mixture.

5. A method for producing a poison resistant active element for a combustible gas sensor comprising the steps of:

forming a filament of electrically conductive material having a resistance varying with temperature into a helical coil;

applying a refractory material to said helical coil and heating said refractory material until sintering takes place to produce a dense gas-tight sheath;

applying a first layer in a liquid mixture form of a combination ceramic material and catalytically active material to said sheath on the helical coil;

curing said first layer;

applying a plurality of alternating layers in a liquid mixture form of a non-catalytic ceramic material and a catalytically active material to said first cured layer on said helical coil;

curing the non-catalytic ceramic material of said plurality of alternating layers and curing the catalytically active material of said plurality of alternating layers to form alternating cured layers of a non-catalytic porous ceramic material and a catalytically active material;

applying a final layer of a liquid mixture containing aluminum chloride and aluminum oxide to the final one of the alternating layers; and heating said liquid mixture layer containing aluminum chloride and aluminum oxide to produce a reaction forming a ceramic layer of aluminum oxide.

6. A method as recited in claim 5 comprising the further step of mixing with water aluminum chloride within the range of 4% to 25% by weight of the mixture and aluminum oxide within the range of 15% to 25% by weight, of the mixture.

* * * * *